US012387815B2

(12) United States Patent
Mourtada et al.

(10) Patent No.: US 12,387,815 B2
(45) Date of Patent: Aug. 12, 2025

(54) VISUAL REPRESENTATIONS OF PEPTIDE SEQUENCES

(71) Applicant: Dana-Farber Cancer Institute, Inc., Boston, MA (US)

(72) Inventors: Rida Mourtada, Brookline, MA (US); Henry D. Herce, Brookline, MA (US); Loren D. Walensky, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1084 days.

(21) Appl. No.: 17/265,642

(22) PCT Filed: Aug. 23, 2019

(86) PCT No.: PCT/US2019/047884
§ 371 (c)(1),
(2) Date: Feb. 3, 2021

(87) PCT Pub. No.: WO2020/041688
PCT Pub. Date: Feb. 27, 2020

(65) Prior Publication Data
US 2021/0304840 A1    Sep. 30, 2021

Related U.S. Application Data

(60) Provisional application No. 62/722,715, filed on Aug. 24, 2018.

(51) Int. Cl.
*G16B 15/20*     (2019.01)
*G16B 15/00*     (2019.01)
*G16C 20/30*     (2019.01)

(52) U.S. Cl.
CPC ............. *G16B 15/20* (2019.02); *G16B 15/00* (2019.02); *G16C 20/30* (2019.02)

(58) Field of Classification Search
CPC .......... G16B 15/20; G16B 15/00; G16C 20/30
See application file for complete search history.

(56) References Cited

U.S. PATENT DOCUMENTS

2007/0021925 A1*  1/2007  Shishiki ................. G16B 15/00
                                                                      702/19
2010/0099614 A1    4/2010  Hodges et al.

OTHER PUBLICATIONS

Simm, Stefan, et al. "50 years of amino acid hydrophobicity scales: revisiting the capacity for peptide classification." Biological research 49 (2016): 1-19. (Year: 2016).*

(Continued)

*Primary Examiner* — Olivia M. Wise
*Assistant Examiner* — Mary C Leverett
(74) *Attorney, Agent, or Firm* — Fish & Richardson P.C.

(57) ABSTRACT

A system for visually representing peptide sequences includes a memory configured to store instructions and a processor to execute the instructions to perform operations. The operations include receiving data representing a peptide sequence. The data includes an index representing a position for each amino acid in the peptide sequence. The operations further include categorizing each amino acid in the peptide sequence and assigning each amino acid a value associated with the category. The operations additionally include determining relationship groups, each group including two amino acids in the peptide sequence, based upon a geometrical structure of the peptide sequence. The operations also include filtering the relationship groups to remove groups based upon the category of at least one of the two amino acids that make up the group; and producing a visual representation that includes a representation of each amino acid of the filtered relationship groups.

12 Claims, 16 Drawing Sheets

Specification includes a Sequence Listing.

(56) References Cited

OTHER PUBLICATIONS

Kapcha, Lauren H., and Peter J. Rossky. "A simple atomic-level hydrophobicity scale reveals protein interfacial structure." Journal of molecular biology 426.2 (2014): 484-498. (Year: 2014).*
Bulka, Blazej, Marie desJardins, and Stephen J. Freeland. "An interactive visualization tool to explore the biophysical properties of amino acids and their contribution to substitution matrices." BMC bioinformatics 7 (2006): 1-9. (Year: 2006).*
Kawashima, Shuichi, et al. "AAindex: amino acid index database, progress report 2008." Nucleic acids research 36.suppl_1 (2007): D202-D205. (Year: 2007).*
Nicolau Jr, Dan V., et al. "Mapping hydrophobicity on the protein molecular surface at atom-level resolution." PLoS One 9.12 (2014) : e114042. (Year: 2014).*
Doncheva, Nadezhda T., et al. "Analyzing and visualizing residue networks of protein structures." Trends in biochemical sciences 36.4 (2011): 179-182. (Year: 2011).*
Lewandowski, Bartosz, et al. "Sequence-specific peptide synthesis by an artificial small-molecule machine." Science 339.6116 (2013): 189-193. (Year: 2013).*
Lee, Ernest Y., et al. "What can machine learning do for antimicrobial peptides, and what can antimicrobial peptides do for machine learning?. " Interface focus 7.6 (2017): 20160153. (Year: 2017).*
Sierra, Josep M., et al. "An overview of antimicrobial peptides and the latest advances in their development." Expert opinion on biological therapy 17.6 (2017): 663-676. (Year: 2017).*
PCT International Preliminary Report on Patentability in International Appln. No. PCT/US2019/047884, dated Mar. 2, 2021, 12 pages.
Berger et al., "Predicting coiled coils by use of pairwise residue correlations," Proc Natl Acad Sci USA, 1995, 92(18):8259-63.
Kovacs et al., "Determination of intrinsic hydrophilicity/hydrophobicity of amino acid side chains in peptides in the absence of nearest-neighbor or conformational effects," Biopolymers, 2006, 84(3):283-97.
PCT International Search Report and Written Opinion in International Appln. No. PCT/US2019/047884, dated Nov. 20, 2019, 14 pages.
Perry et al., "Contiguous hydrophobic and charged surface patches in short helix-constrained peptides drive cell permeability," Org Biomol Chem., 2018, 16(3):367-371.
Mourtada, "Engineering Membrane-Selective Antibiotic Peptides to Combat Multidrug Resistance," Dissertation for the degree of Doctor of Philosophy in Medical Engineering and Medical Physics, Massachusetts Institute of Technology, Jun. 2018, 189 pages.

\* cited by examiner

Relationship Groups (i+3 and i+4)

Hydrophilic Amino Acids:

wamino = {"Q", "N", "S", "C", "R", "D", "H", "K", "E"};

{{X, 1, 29.5} → {X, 5, 29.5}, {I, 2, 22.4} → {L, 6, 24.2}, {G, 3, 0.} → {H, 7, 3.4},
{X, 5, 29.5} → {A, 9, 3.9}, {K, 10, 1.1},
{H, 7, 3.4} → {K, 11, 1.1}, {A, 9, 3.9} → {G, 13, 0.},
{K, 10, 1.1} → {K, 14, 1.1}, {A, 15, 3.9} → {F, 16, 29.9},
{G, 13, 0.} → {V, 17, 14.4}, {K, 18, 0.},
{F, 16, 29.9} → {I, 20, 22.4}, {V, 17, 14.4} → {B, 21, 25.6}, {I, 2, 22.4} → {X, 5, 29.5},
{G, 3, 0.} → {L, 6, 24.2}, {V, 17, 14.4} → {I, 20, 22.4},
{L, 6, 24.2} → {A, 9, 3.9},
{A, 9, 3.9} → {F, 12, 29.9}, {G, 13, 0.} → {F, 16, 29.9},
{F, 12, 29.9} → {A, 15, 3.9}, {G, 13, 0.},
{A, 15, 3.9} → {G, 18, 0.},
{G, 18, 0.} → {B, 21, 25.6}}

```
For[i = 1, i ≤ Dimensions[wamino][[1]], i++, {ii = DeleteCases[ii, (wamino[[i]], _, _) → _],
ii = DeleteCases[ii, _ → (wamino[[i]], _, _)]}];
```

FIG. 7

Filtered Data Structure

{{X, 1, 29.5} → {X, 5, 29.5}, {I, 2, 22.4} → {L, 6, 24.2},
{X, 5, 29.5} → {A, 9, 3.9}, {A, 9, 3.9} → {G, 13, 0.}, {F, 12, 29.9} → {F, 16, 29.9},
{G, 13, 0.} → {V, 17, 14.4}, {F, 16, 29.9} → {I, 20, 22.4}, {V, 17, 14.4} → {B, 21, 25.6},
{I, 2, 22.4} → {X, 5, 29.5}, {G, 3, 0.} → {L, 6, 24.2}, {L, 6, 24.2} → {A, 9, 3.9},
{A, 9, 3.9} → {F, 12, 29.9}, {F, 12, 29.9} → {A, 15, 3.9}, {G, 13, 0.} → {F, 16, 29.9},
{A, 15, 3.9} → {G, 18, 0.}, {V, 17, 14.4} → {I, 20, 22.4}, {G, 18, 0.} → {B, 21, 25.6}}

Function Call

```
FormPage[
 {"HMM & Lyticity Index" -> <|"Interpreter" -> Restricted["Integer", {1, 36}],
  "Control" -> InputField, "Help" -> "Choose a peptide from 1-36",
  "Hint" -> "write something"|>}, hydrophobicitynetworkmap[#"HMM & Lyticity Index"] &]
```

FIG. 12

SEQUENCE LISTING

```
<160> NUMBER OF SEQ ID NOS: 2

<210> SEQ ID NO 1
<211> LENGTH: 23
<212> TYPE: PRT
<213> ORGANISM: Artificial Sequence
<220> FEATURE:
<223> OTHER INFORMATION: synthetic peptide
<220> FEATURE:
<221> NAME/KEY: X
<222> LOCATION: (1)..(1)
<223> OTHER INFORMATION: (S)-2-(4-pentenyl)alanine
<220> FEATURE:
<221> NAME/KEY: X
<222> LOCATION: (5)..(5)
<223> OTHER INFORMATION: (S)-2-(4-pentenyl)alanine

<400> SEQUENCE: 1
```

```
Xaa Ile Gly Lys Xaa Leu His Ser Ala Lys Lys Phe Gly Lys Ala Phe
1               5                   10                  15

Val Gly Glu Ile Asx Asn Ser
            20

<210> SEQ ID NO 2
<211> LENGTH: 23
<212> TYPE: PRT
<213> ORGANISM: Artificial Sequence
<220> FEATURE:
<223> OTHER INFORMATION: synthetic peptide
<220> FEATURE:
<221> NAME/KEY: X
<222> LOCATION: (1)..(1)
<223> OTHER INFORMATION: (S)-2-(4-pentenyl)alanine
<220> FEATURE:
<221> NAME/KEY: X
<222> LOCATION: (5)..(5)
<223> OTHER INFORMATION: (S)-2-(4-pentenyl)alanine

<400> SEQUENCE: 2

Xaa Ile Gly Lys Xaa Leu His Ser Glx Lys Lys Phe Gly Lys Ala Phe
1               5                   10                  15

Val Gly Glu Ile Asx Asn Ser
            20
```

VISUAL REPRESENTATIONS OF PEPTIDE SEQUENCES

CROSS-REFERENCE TO RELATED APPLICATIONS

This application is a National Phase entry of International Patent Application No. PCT/US2019/047884, filed on Aug. 23, 2019, which claims priority to Application No. U.S. 62/722,715, filed on Aug. 24, 2018, the disclosures of which are hereby incorporated by reference in their entireties.

SEQUENCE LISTING

This application contains a Sequence Listing that has been submitted electronically as an ASCII text file named 00530-0350US1_ST25.txt. The ASCII text file, created on Nov. 25, 2024, is 1,254 bytes in size. The material in the ASCII text file is hereby incorporated by reference in its entirety.

BACKGROUND

This description relates to visually representing peptide sequences. Having a graphical representation of the peptide sequences is especially helpful in drug development where therapeutic peptide drug design has become increasingly widespread.

Peptides are complex biomolecules with unique properties, which are afforded by the side chains of the amino acids within their sequences. Due to their ability to interact with a wide variety of biological targets with specificity and potency, peptides are recognized as having large growth potential in therapeutics. Modifying the peptides' sequences is often used to imbue various properties, such as increased stability, and lower toxicity, depending on the desired application of the peptides. Graphically representing peptide sequences can help with understanding various characteristics of the peptide sequences.

SUMMARY

The systems and techniques described can aid individuals such as researchers, drug developers, etc. with therapeutic peptide drug design. Visual representation of peptide sequences in a network format can emphasize relationships between amino acids that are close together in three-dimensional (3D) space. The visual representation allows researchers to quickly recognize the structure of the peptide and identify characteristics of connections between amino acids in the peptide sequence. This can improve efficiency of peptide design by allowing researchers to understand interactions between the amino acids and the overall structure of the peptide sequence.

A graphical map of the peptide's amino acid relationships, where nodes represent amino acids and edges represent connections with amino acid neighbors, can improve efficiency of peptide design by allowing users to quickly recognize the structure of the peptides, understand interactions between peptides, etc. In certain implementations, the peptide's hydrophobic amino acid relationships can be highlighted and used in calculating a lyticity index, which is a predictor of undesirable lytic behavior. This tool can help users with the design effort by assisting in the selection of amino acid substitutions, insertions, deletions, etc. for reducing toxicity. Combining this technique with other metrics besides hydrophobicity and lyticity index (e.g. cationic charge density) can create networks that provide different useful information (e.g. antimicrobial properties). Having a graphical representation of peptide sequences that highlights interactions between amino acids and characterizes properties of peptides, can substantially reduce the amount of time, resources, etc. needed when studying protein folding, designing pharmaceuticals, understanding biochemical pathways, etc.

In one aspect, a computing device implemented method includes receiving data representing a peptide sequence. The data includes an index for each amino acid included in the peptide sequence, and each index represents a position of the corresponding amino acid in the peptide sequence. The method further includes, for each amino acid in the peptide sequence, determining a category for the amino acid and a value associated with the category for the amino acid; and determining one or more relationship groups of the amino acids in the peptide sequence based upon a geometrical structure of the peptide sequence, in which each relationship group includes two of the amino acids in the peptide sequence. The method further includes filtering the one or more relationship groups of the amino acids in the peptide sequence to remove one or more of the relationship groups based upon the category of at least one of the two amino acids of the respective relationship group; and producing a visual representation that includes a representation of each amino acid of the filtered relationship groups.

Implementations may include one or more of the following features. The computing device implemented method can further include determining a peptide index from the values associated with the amino acids of the filtered relationship groups, the peptide index being presented by the visual representation. Determining the peptide index can include summing values associated with amino acids for each filtered relationship group or summing values associated with amino acids for all of the filtered relationship groups. The category for the amino acids can include hydrophobicity or hydrophilicity. The value associated with the category for the amino acid can include a level of hydrophobicity or a level of hydrophilicity. Determining one or more relationship groups of the amino acids in the peptide sequence based upon a geometrical structure of the peptide sequence can include determining two amino acids separated by two or three amino acids. The visual representation can include a graphical representation of a relationship between a pair of amino acids, or a graphical representation of the hydrophobicity of the pair of amino acids.

In another aspect, a system includes a memory configured to store instructions and a processor to execute the instructions to perform operations. The operations include receiving data representing a peptide sequence. The data includes an index for each amino acid included in the peptide sequence, and each index represents a position of the corresponding amino acid in the peptide sequence. The operations further include, for each amino acid in the peptide sequence, determining a category for the amino acid and a value associated with the category for the amino acid; and determining one or more relationship groups of the amino acids in the peptide sequence based upon a geometrical structure of the peptide sequence, in which each relationship group includes two of the amino acids in the peptide sequence. The operations further include filtering the one or more relationship groups of the amino acids in the peptide sequence to remove one or more of the relationship groups based upon the category of at least one of the two amino acids of the respective relationship group; and producing a visual representation that includes a representation of each amino acid of the filtered relationship groups.

Implementations may include one or more of the following features. The operations can further include determining a peptide index from the values associated with the amino acids of the filtered relationship groups, the peptide index being presented by the visual representation. Determining the peptide index can include summing values associated with amino acids for each filtered relationship group or summing values associated with amino acids for all of the filtered relationship groups. The category for the amino acids can include hydrophobicity or hydrophilicity. The value associated with the category for the amino acid can include a level of hydrophobicity or a level of hydrophilicity. Determining one or more relationship groups of the amino acids in the peptide sequence based upon a geometrical structure of the peptide sequence can include determining two amino acids separated by two or three amino acids. The visual representation can include a graphical representation of a relationship between a pair of amino acids, or a graphical representation of the hydrophobicity of the pair of amino acids.

In another aspect, one or more computer-readable media store instructions that are executable by a processing device. Upon such execution, the instructions cause the processing device to perform operations that include receiving data representing a peptide sequence. The data includes an index for each amino acid included in the peptide sequence, and each index represents a position of the corresponding amino acid in the peptide sequence. The operations further include, for each amino acid in the peptide sequence, determining a category for the amino acid and a value associated with the category for the amino acid; and determining one or more relationship groups of the amino acids in the peptide sequence based upon a geometrical structure of the peptide sequence, in which each relationship group includes two of the amino acids in the peptide sequence. The operations further include filtering the one or more relationship groups of the amino acids in the peptide sequence to remove one or more of the relationship groups based upon the category of at least one of the two amino acids of the respective relationship group; and producing a visual representation that includes a representation of each amino acid of the filtered relationship groups.

Implementations may include one or more of the following features. The operations can further include determining a peptide index from the values associated with the amino acids of the filtered relationship groups, the peptide index being presented by the visual representation. Determining the peptide index can include summing values associated with amino acids for each filtered relationship group or summing values associated with amino acids for all of the filtered relationship groups. The category for the amino acids can include hydrophobicity or hydrophilicity. The value associated with the category for the amino acid can include a level of hydrophobicity or a level of hydrophilicity. Determining one or more relationship groups of the amino acids in the peptide sequence based upon a geometrical structure of the peptide sequence can include determining two amino acids separated by two or three amino acids. The visual representation can include a graphical representation of a relationship between a pair of amino acids, or a graphical representation of the hydrophobicity of the pair of amino acids.

These and other aspects, features, and various combinations may be expressed as methods, apparatus, systems, means for performing functions, program products, etc.

Other features and advantages will be apparent from the description and the claims.

DESCRIPTION OF DRAWINGS

FIG. 6 illustrates an exemplary data structure for storing relationship groups of amino acids of the peptide sequence.

FIG. 7 illustrates filtering the data structure to remove relationship groups including hydrophilic amino acids.

FIG. 12 is a function call to initiate operations of a peptide manager to present the user prompt shown in FIG. 3.

DETAILED DESCRIPTION

Figure 1:
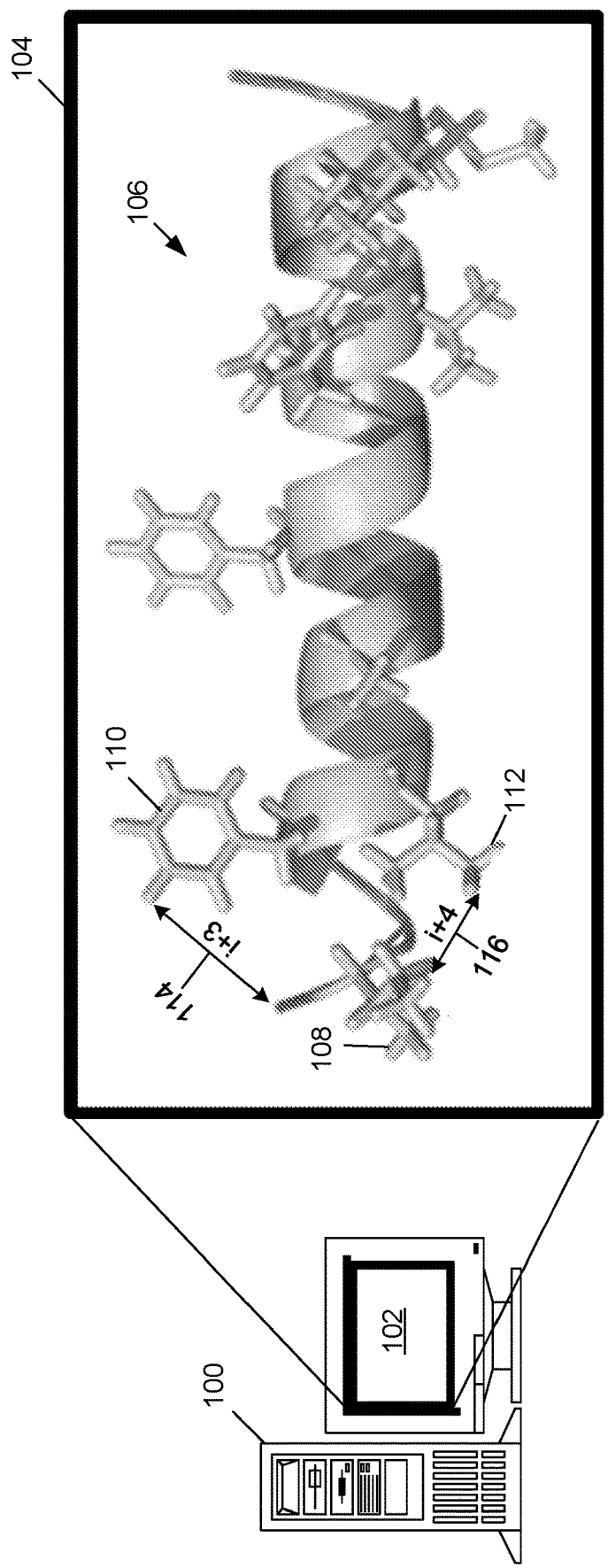
FIG. 1 is a 3D structural representation of portions of a peptide sequence presented by a computing device.

Referring to FIG. 1, a computing device (e.g., a computer system 100) conveys information about chemical bonds such as information about peptide sequences. In general, a peptide can be considered as including any sequence of amino acids connected to one another by peptide bonds. A peptide sequence can be considered as including a listing of amino acids from the N-terminus to the C-terminus of the peptide, such that the peptide sequence is representative of the primary structure of the peptide. Representing peptide sequences can assist designers in various applications including predicting protein folding configurations, designing pharmaceuticals, and understanding biochemical pathways. In particular, understanding the interactions between the amino acids of a peptide when the peptide is folded in three-dimensional space can assist in these applications. These interactions arise due to the secondary, tertiary, and quaternary structures of peptides. Visual representations of peptides can assist with providing an understanding of the overall structure of the peptide along with the interactions of amino acids that are in close proximity in three-dimensional space. Additionally, such visual representations can assist with understanding other characteristics of the peptide sequence such as toxicity. Such visual representations can take one or more forms; for example, peptides and interactions of associated amino acids can be graphically represented in three-dimensional (3D) space by using a network representation in which nodes represent amino acids and edges of the network represent interactions between amino acids located in close proximity in three-dimensional space. Various types of implementations can be utilized for generating such graphical representations; for example, such representations can be implemented in executable instructions provided by software-based processes, hardware implementations, combinations of software and hardware, etc.

As illustrated in the figure, the computer system 100 includes a display 102 that presents a representation 104 in 3D of a peptide sequence 106 that includes amino acids 108, 110, 112. Along with providing a general understanding of the structure of the peptide sequence, the representation can provide an understanding of characteristics of the peptide sequence. Such information can be helpful in drug development where therapeutic peptide drug design is becoming more widespread and peptides are recognized for their large growth potential in therapeutics due to their specificity and potency. Further, the representation 104 can graphically represent interactions between the amino acids included in the peptide sequence. Representing such amino acid interactions can be used for designing antimicrobial peptides (AMPs) that are generally minimally toxic to human tissues while retaining antimicrobial potency. Many antimicrobial peptides (AMPs), similarly to cationic antibiotics such as colistin, polymyxin b, and gentamicin, cause nephrotoxicity over the course of treatment. Thus, one approach for designing AMPs is to first minimize toxicity, and then select AMPs with suitable antimicrobial potency.

In some experimental testing (e.g., testing of StAMP51), a stapled antimicrobial peptide and re-engineered variants show that disrupting hydrophobic patches of a peptide in its three-dimensional configuration (e.g., by replacing norleucine residues with alanine) can reduce lytic (i.e. toxic) activity, but also reduces antimicrobial potency. However, by increasing cationic properties on the hydrophilic face of a peptide in its three-dimensional configuration, similar potency to unaltered StAMP51 can be achieved with markedly reduced lytic activity toward human kidney tissue cells (pRPTECs). These results suggest that a design goal for engineering AMPs is to disrupt hydrophobic patches on the three-dimensional peptide structure and increase cationic residues on the hydrophilic face.

In order to disrupt hydrophobic patches and reduce (e.g., minimize) the lyticity of a peptide such as StAMP51, one can refer to a network representation of hydrophobic interactions between amino acids of the peptide that are located in close proximity in three-dimensional space.

As illustrated in the figure, the representation 104 depicts the 3D structure representation of the peptide 106. This representation 104 shows the alpha-helical structure of the peptide 106 and some sidechains of the amino acid residues. The 3D structure representation of the peptide 106 further shows that given the alpha-helical structure of the peptide, an amino acid of index i in the peptide sequence is most closely located to amino acids of i+3 (highlighted with arrowed line 114) and i+4 (highlighted by arrowed line 116) in three-dimensional space. However, due to the peptide's three-dimensional geometry, the representation 104 is unable to show all of the amino acids comprising the peptide sequence simultaneously on the two-dimensional display 102. In addition, the 3D representation 104 of the peptide 106 does not provide information about the interactions between each amino acid and the amino acids most proximal to it in three-dimensional space. Thus, the 3D structure in representation 104 of the peptide 106 is unable to accurately identify hydrophobic patches of the peptide 106 in order to disrupt the hydrophobic patches and minimize lyticity of the peptide 106.

Figure 2:
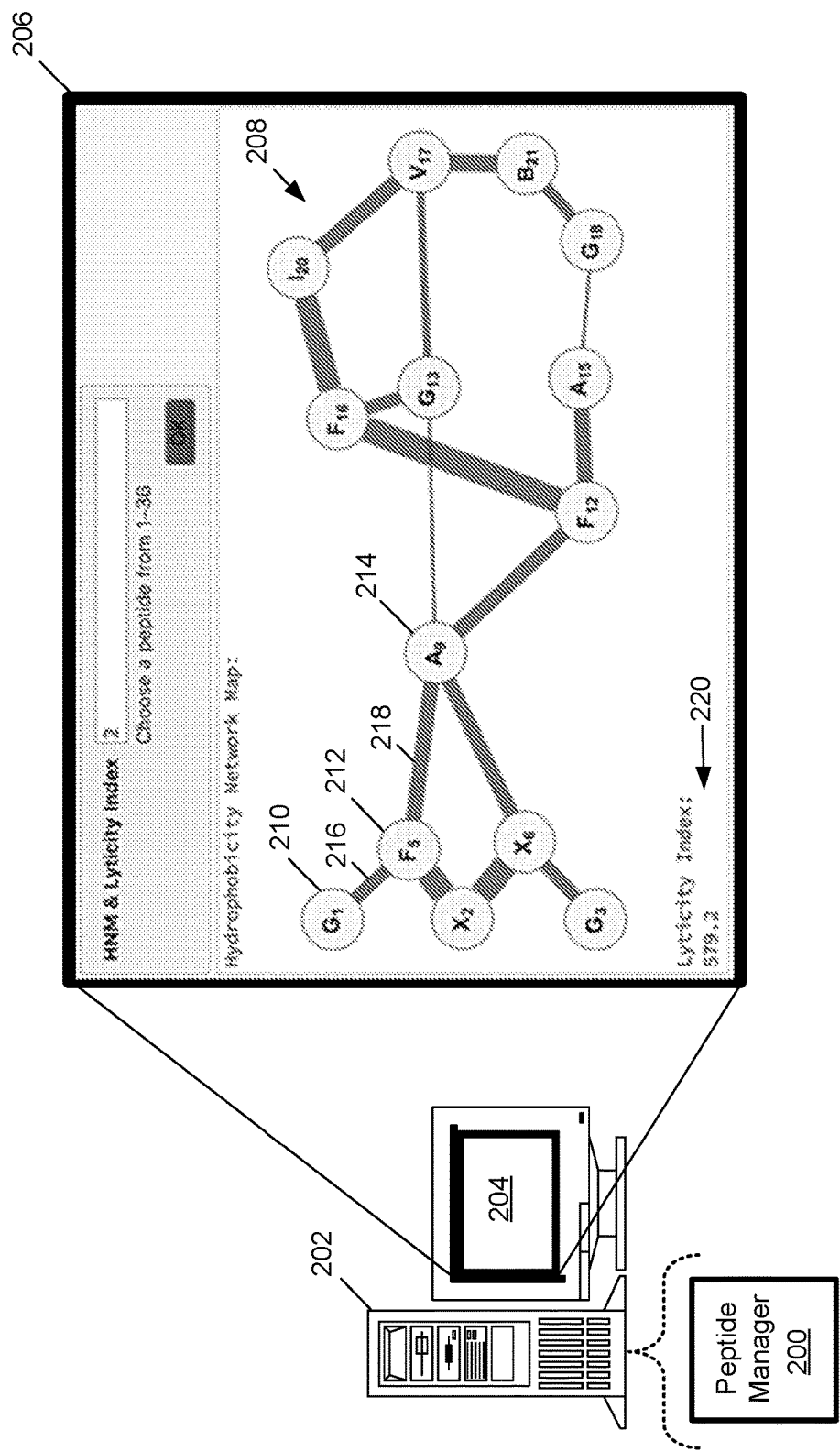
FIG. 2 is a network map representation of a complete peptide sequence and a metric presented by a computing device.

Referring to FIG. 2, to convey a complete information set for a peptide and associated amino acids, a peptide manager 200 is executed by a computing device (e.g., computer system 202) to present (on a display 204) a graphical representation 206 of the information. In this example, the visual representation 206 includes a hydrophobicity network map 208, in which each node (e.g., nodes 210, 212, 214) of the hydrophobicity network map 208 represents an amino acid of the peptide (e.g., peptide 106 shown in FIG. 1). For this example, amino acids that do not contribute to a hydrophobic patch of the peptide are not presented. An amino acid is considered to not contribute to the hydrophobic patch of the peptide if its side chain is hydrophilic and/or charged. Such visual representations can represent various categories of the peptide sequences; for example, as mentioned above a hydrophobic amino acid category may be used to represent peptides. Other categories associated with hydrophilic amino acids, cationic charge density, anionic charge density, etc. may be used to represent peptides. In some cases, the graphical representation 206 may simultaneously use multiple categories to represent peptides (e.g., by using different colors, different line types, etc.). For example, hydrophobic interactions could be shown with red edges connecting the corresponding nodes while hydrogen bonding interactions can be simultaneously shown with green edges in a single graphical representation 206.

In general, the hydrophobicity network map 208 represents relationships between each amino acid and the amino acids most proximal to it in three-dimensional space by representing these relationships with a graphical edge connecting the corresponding nodes. In this example, due to the alpha-helical nature of the peptide structure, an edge connects each amino acid with other amino acids located 3 and 4 indices apart from it in the peptide sequence (e.g., i+3 and i+4), as long as they contribute to the hydrophobic patch of the peptide. For example, as illustrated in the figure, the node 210 represents an amino acid and an edge 216 connects to the node 212 that represents another amino acid. Similarly, an edge 218 connects the amino acid represented by node 212 to the amino acid represented by node 214.

Unlike two-dimensional projections of 3D structure representation 104, the hydrophobicity network map 208 is a two-dimensional visual representation that is able to present all the amino acids that contribute to the hydrophobic patch of the peptide 106 simultaneously on the two-dimensional on-screen display 104. Moreover, the hydrophobicity network map 208 has the advantage of being able to provide information about the interactions between each amino acid and the amino acids most proximal to it in three-dimensional space. In the example shown in FIG. 2 each edge thickness corresponds to a sum of the hydrophobicity values of the amino acids represented by the connected nodes, thus representing information about the hydrophobic interactions between them. The information about the hydrophobic interactions across the peptide is further characterized by a quantitative metric called the lyticity index 220 (e.g., having a value of 579.2 as shown in the figure), which is displayed alongside the hydrophobicity network map 208 and is described in further detail below.

Figure 3:
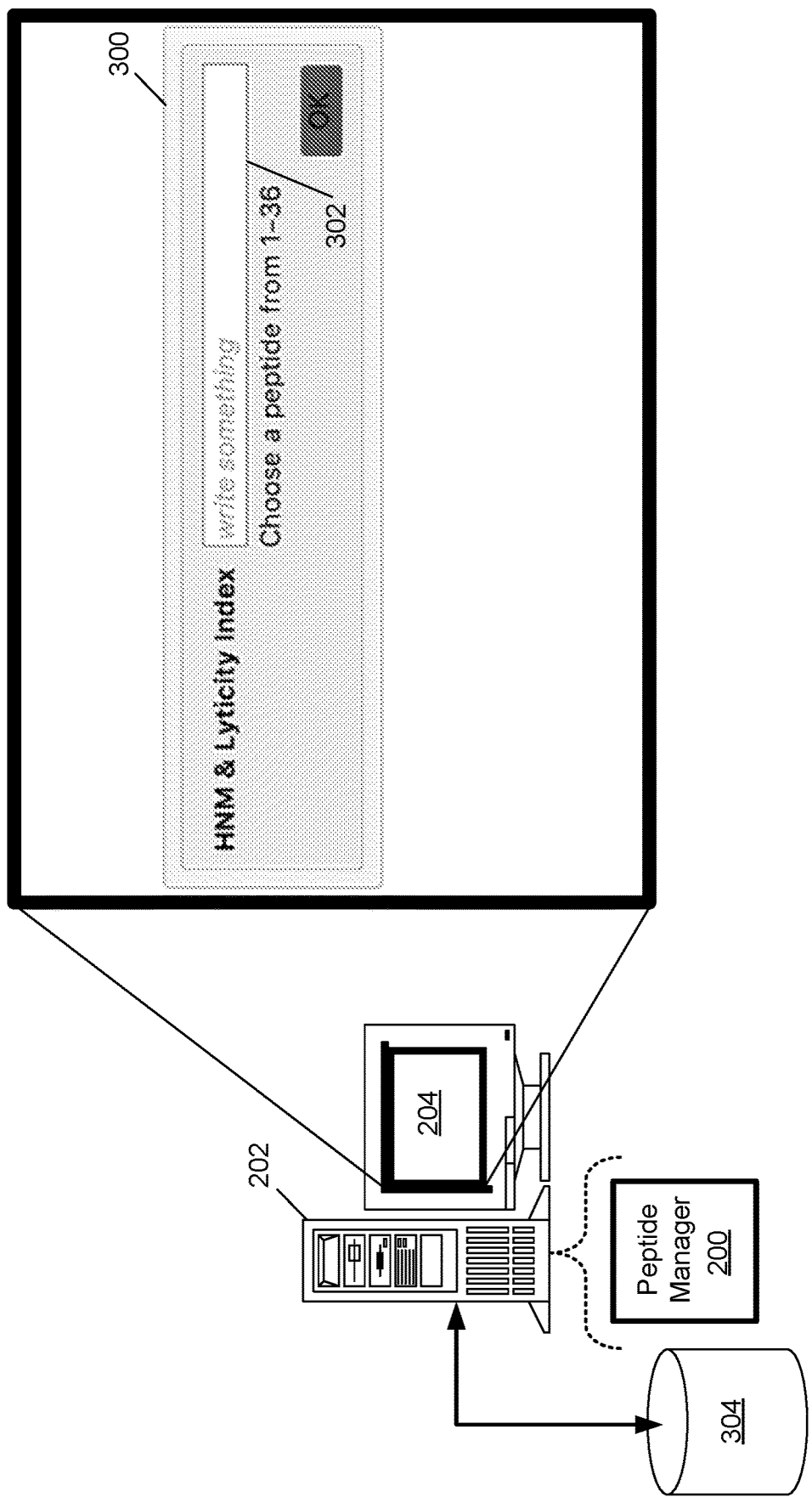
FIG. 3 is a user prompt, presented by a computing device, for visually representing a peptide sequence.

Referring to FIG. 3, to generate a visual representation of a peptide such as the hydrophobicity network map 208 (shown in FIG. 2), one or more techniques may be employed. For example, one or more software processes may be executed by a computing device to perform operations to produce such graphical representations. Such operations may include guiding a user through one or more interfaces to collect information, allow preferences selections, and presenting graphics such as network maps. In the example shown in the figure, the peptide manager 200 (executed on the computer system 202 having the display 204) causes an interface 300 to be presented that prompts a user for information. Through this interface 300, a peptide can be selected through user interactions; for example, a numerical value can be entered into a field 302 included in the interface 300. Other user interaction techniques may also be used; for example, one or more menus may be presented for the user to select a peptide for presentation. For instances in which the data representing a peptide of interest is not stored, the interface 300 could direct the user to one or more other software processes for peptide development (e.g., a peptide modeling application) to create a representation of a peptide and storing representative data (e.g., in a storage device 304).

For the examples described herein, the user selects a peptide in the interface 300 by entering a string of characters into the field 302. The string of characters can represent a peptide in FASTA format (e.g., using standard IUB/IUPAC amino acid codes). However, modifications and additions can be made to the standard IUB/IUPAC amino acid codes to allow for "stapling" amino acids. Namely, in the examples given below, the character "X" is used to represent the stapling amino acid (S)-2-(4-pentenyl)alanine and the character "8" is used to represent (R)-2-(7-octenyl)alanine. In some implementations, the peptide manager 200 can enforce one or more rules for the input entered in the field 302. For example, in order to reflect the stapling mechanism of (S)-2-(4-pentenyl)alanine, the peptide manager 200 can require that the character "X" must always be spaced 4 characters away from another "X" or 7 characters away from an "8". In some implementations, if an unrecognized character or invalid string is entered into the field 302, the peptide manager 200 can cause an error message to be displayed to the user.

Once a valid peptide has been identified, data representing the peptide of interest can be retrieved, for example, from one or more local sources (e.g., the storage device 304), one or more remote sources (e.g., via a network, the Internet, etc.), etc. Provided the data, a network map of the peptide can be produced by the peptide manager 200 and presented on the display 204. The map may also be stored in the storage device 304 for later retrieval by the peptide manager 200.

Figure 4:
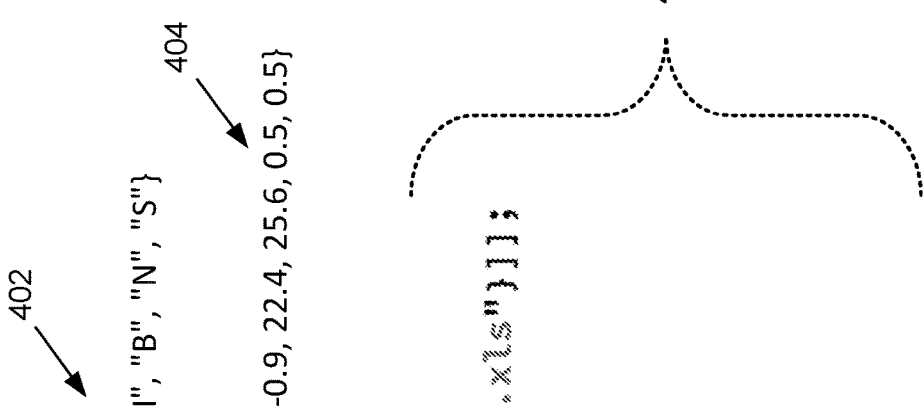
FIG. 4 illustrates a vector of amino acids of a peptide sequence, a vector of hydrophobic data, and instructions for retrieving data.

To produce hydrophobicity network maps, calculate lyticity indices, etc. the peptide manager 200 can employ various types of operations, functions, etc. Referring to FIGS. 4-10, an example peptide sequence is used to illustrate the operations of the peptide manager 200 to determine and provide this information. Referring to FIG. 4, a data importation operation of the peptide manager 200 can be implemented using example data importation instructions 400. Executed, the instructions 400 extract data (e.g., from an MS-Excel spreadsheet called "Data Set.xls" stored on the storage device 304) and enters the data (e.g., into vector format). In this example, the instructions 400 produce two vectors; a first vector 402 includes data that represents the peptide sequence of interest, where each character (e.g., a letter of the alphabet) represents an individual amino acid and the characters are placed in sequential order according to the primary structure of the peptide. A second vector 404 is a vector containing the hydrophobicity values of the amino acids in the first vector 402, where the sequential order is maintained. As such, read from left to right, the first character of the first vector 402 (e.g., the letter "X") has a corresponding hydrophobicity value (e.g., 29.5) provided by the first element of the second vector 404. Similarly, the second character of the first vector 402 (e.g., the letter "I") has a hydrophobicity value (e.g., 22.4) that is provided by the second element of the second vector 404. This correspondence continues for the remaining elements of the first vector 402 and the second vector 404; however, other type of protocols, data structures, etc. may be employed. For example, in some cases, a single vector (e.g., a concatenation of the two vectors described above) may be used to represent both the amino acid codes and the hydrophobicity values of the peptide sequence. In general, the data related to the peptide sequence of interest can be stored in any suitable data structure including lists, 2D arrays, multidimensional matrices, dictionaries, and hashtables, among others. One or more sources may be used for values such as hydrophobicity values, for example; values can be utilized from "Determination of Intrinsic Hydrophilicity/Hydrophobicity of Amino Acid Side Chains in Peptides in the Absence of Nearest Neighbor or Conformation Effects," Biopolymers 84(3): 283-97, January 2006, which is incorporated in its entirety by reference herein. In some cases, the hydrophobicity value for (S)-2-(4-pentenyl)alanine can be estimated by combining (e.g. summing) the hydrophobicity values for alanine and norleucine. In some cases, the hydrophobicity value for (R)-2-(7-octenyl)alanine can be estimated by combining the hydrophobicity values for one alanine and two leucine residues.

In some arrangements, the peptide manager 200 may use the information provided by the first vector 402, the second vector 404, etc. to determine one or more categories of an amino acid. For example, the values provided in second vector 402 (e.g., hydrophobicity values) may be used to identify a corresponding amino acid (in the first vector 402) as being hydrophobic or hydrophilic. The information contained in the first vector 402 may also be used to determine the category of each amino acid. For example, based upon the character used to represent the amino acid in the first vector 402, the peptide manager 200 may be able to determine if the corresponding amino acid is a member of a hydrophobic category or a hydrophilic category. Other types of categories may be determined and used to identify different characteristics of the amino acids; for example, one or more categories may be determined from cationic charge densities by the peptide manager 200.

Figure 5:
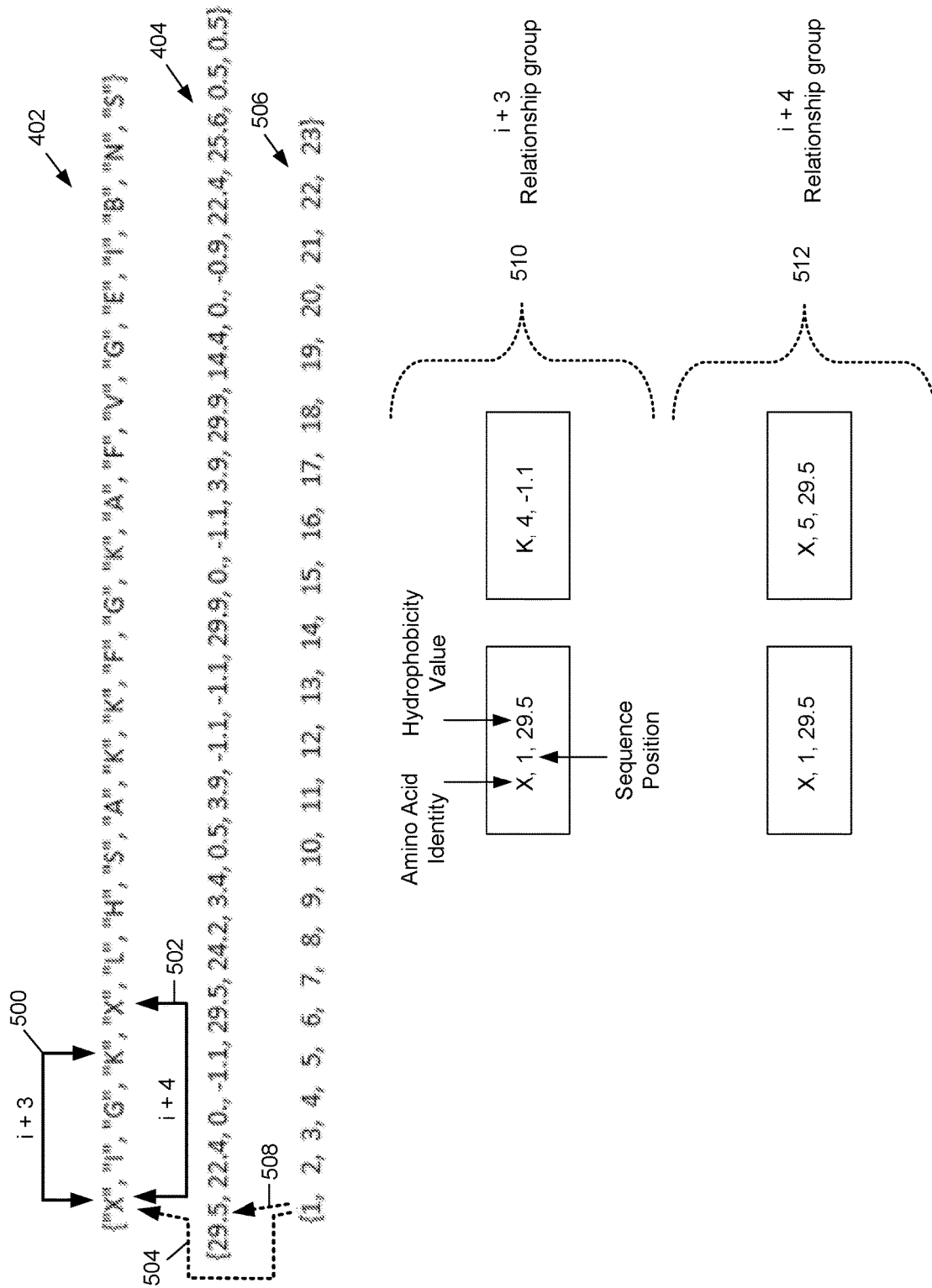
FIG. 5 illustrates determining relationship groups of the amino acids of the peptide sequence.

Referring to FIG. 5, with the first and second vectors 402, 404 produced, the peptide manager 200 executes relationship grouping operations 500. Due to the alpha-helical structure of the peptide, in three-dimensional space each amino acid in a peptide is generally located most closely to the amino acids located 3 and 4 indices apart from it in the peptide sequence. As such, a relationship group is created between each amino acid of index i and the amino acids of index i+3 and i+4. In other examples, larger or smaller separations between the amino acids may be employed (e.g., for protein structures such as beta sheets, disulfide bridges, etc.). In the illustrated example, relationship groupings are shown for the first amino acid represented (by the letter "X") in the first vector 402 that represents the peptide sequence. This first amino acid "X" is located at the first sequence position, or index, in the first vector 402 (as highlighted by dashed arrow 504 with respect to a vector 506 of position values). The first amino acid "X" also has a hydrophobicity of 29.5, as provided by the value of the first sequence position in the second vector 404 (as highlighted by dashed arrow 508 with respect to the vector 506).

To form an i+3 relationship group (illustrated by bracket 500), the amino acid identity (letter "X"), hydrophobicity value, and sequence position of the amino acid are stored with the amino acid identity, hydrophobicity value, and sequence position of the amino acid located 3 indices after "X". Since "X" is located at the first sequence position, the i+3 relationship group is formed between "X" and the amino acid at the fourth (i+3) index, which, in the example shown, is amino acid "K". In the figure, data associated this i+3 relationship group is shown with graphical representation 510.

To form an i+4 relationship group (illustrated by bracket 502), the amino acid identity, hydrophobicity value, and sequence position of "X" is stored with the amino acid identity, hydrophobicity value, and sequence position of the amino acid located 4 indices after "X". Since "X" is located at the first sequence position, a relationship group is formed between "X" and the amino acid at the fourth (i+4) index, which, in the example shown, is also amino acid "X". In the figure, the i+4 relationship group is shown with graphical representation 512.)

This process is repeated for every amino acid in the first vector 402 until the i+3 or i+4 index exceeds the length of the first vector 402. In general, if the first vector 402 that represents the peptide sequence is of length n, the number of relationship groups formed is equal to 2n−7, with n−3 relationship groups between the amino acids of index i and i+3, and n−4 relationship groups between the amino acids of index i and i+4.

Figure 6:
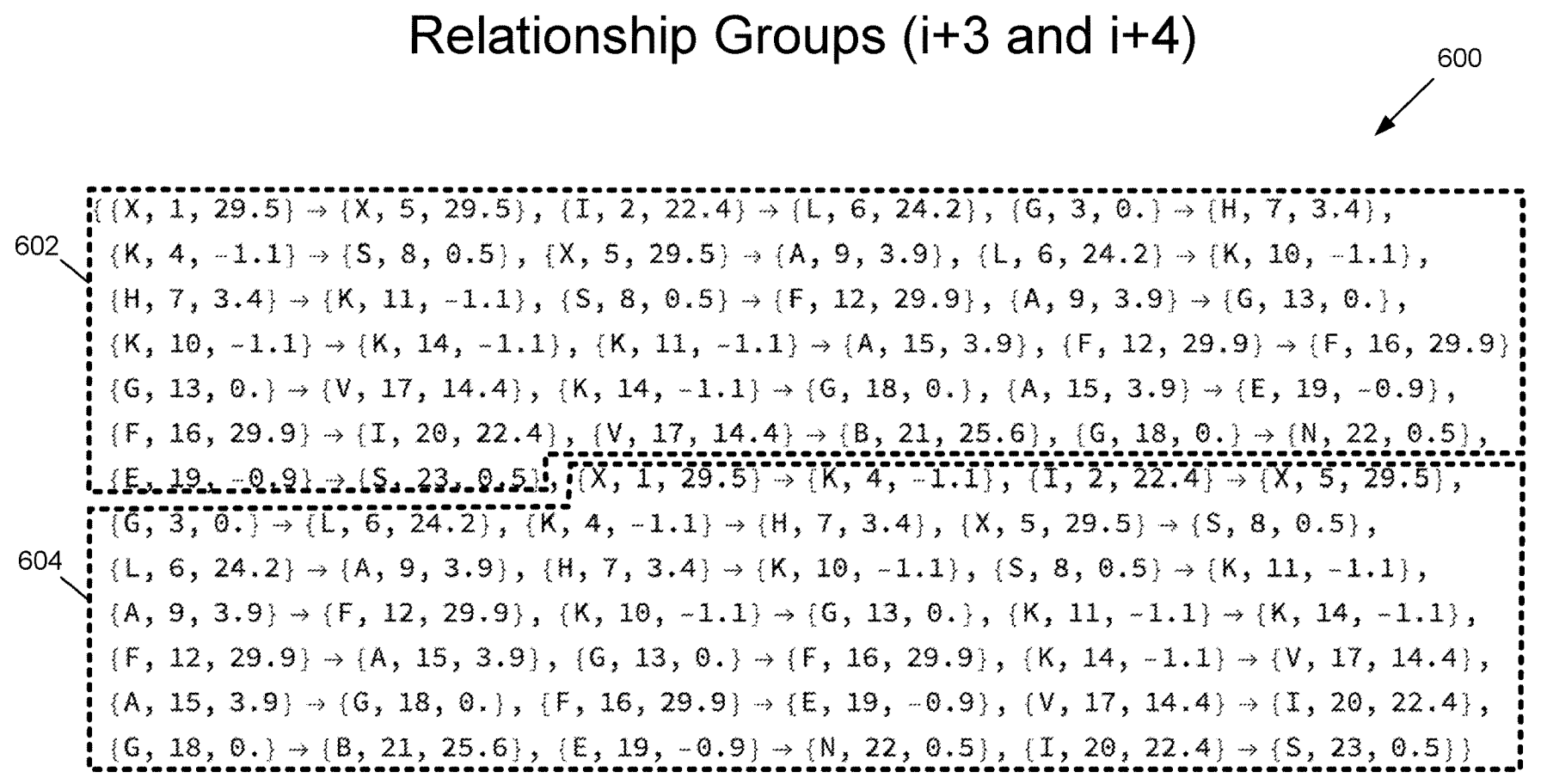

Referring to FIG. 6, using the first and second vectors 402, 404 (representing the peptide sequence and the hydrophobicity), the peptide manager 200 can produce one or more data structures that contain the relationship groups. As illustrated, a data structure 600 includes each of the relationship groups for amino acids with indices i and i+4, as graphically highlighted with dashed box 602. The data structure 600 also includes the relationship groups for amino acids with indices i and i+3, as graphically highlighted with dashed box 604. While various formats may be used for each of the relationship groups (i.e., the i+4 groups, and the i+3 groups), the following format is employed in this example:

(Amino acid identity 1, Index 1, Hydrophobicity value 1)→(Amino acid identity 2, Index 2, Hydrophobicity value 2).

Figure 8:
FIG. 8 illustrates a filtered data structure that includes relationship groups having hydrophobic amino acids.

Referring to FIG. 7, upon determining the relationship groups (e.g., the i+3 and i+4 relationship groups), the peptide manager 200 is capable of processing the data of these groups. For example, if a researcher is interested in identifying the hydrophobic regions of a peptide, the researcher may only be interested in relationship groups in which both amino acids are hydrophobic. For relationship groups that do not solely include hydrophobic amino acids, they may be filtered out by the peptide manager 200. Filtering the groups can result in non-hydrophobic amino acids being removed. For example, a vector 700 of hydrophilic amino acids may be provided to the peptide manager 200 (e.g., retrieved from storage device 304) for removing relationship groups (from the relationship groups of the data structure 600) that have at least one hydrophilic amino acid. In this example, the vector of all hydrophilic amino acids 700 is entitled "wamino" and is provided to the peptide manager 200. To remove the hydrophilic amino acids from the relationship groups of data structure 600, the peptide manager 200 executes instructions 702 that use the vector 700 of hydrophilic amino acids; however other types of instructions, functions, etc. may be used. Through the processing, the peptide manager 704 produces another data structure 704, within which graphical bars are used to represent which relationship groups have been filtered out (i.e., groups that contain at least one of the hydrophilic amino acids 700 are removed). Referring to FIG. 8, based upon the removal of relationship groups containing one or more hydrophilic amino acids, a filtered data structure 800 is produced, which includes only relationship groups where both amino acids are hydrophobic.

Figure 9:
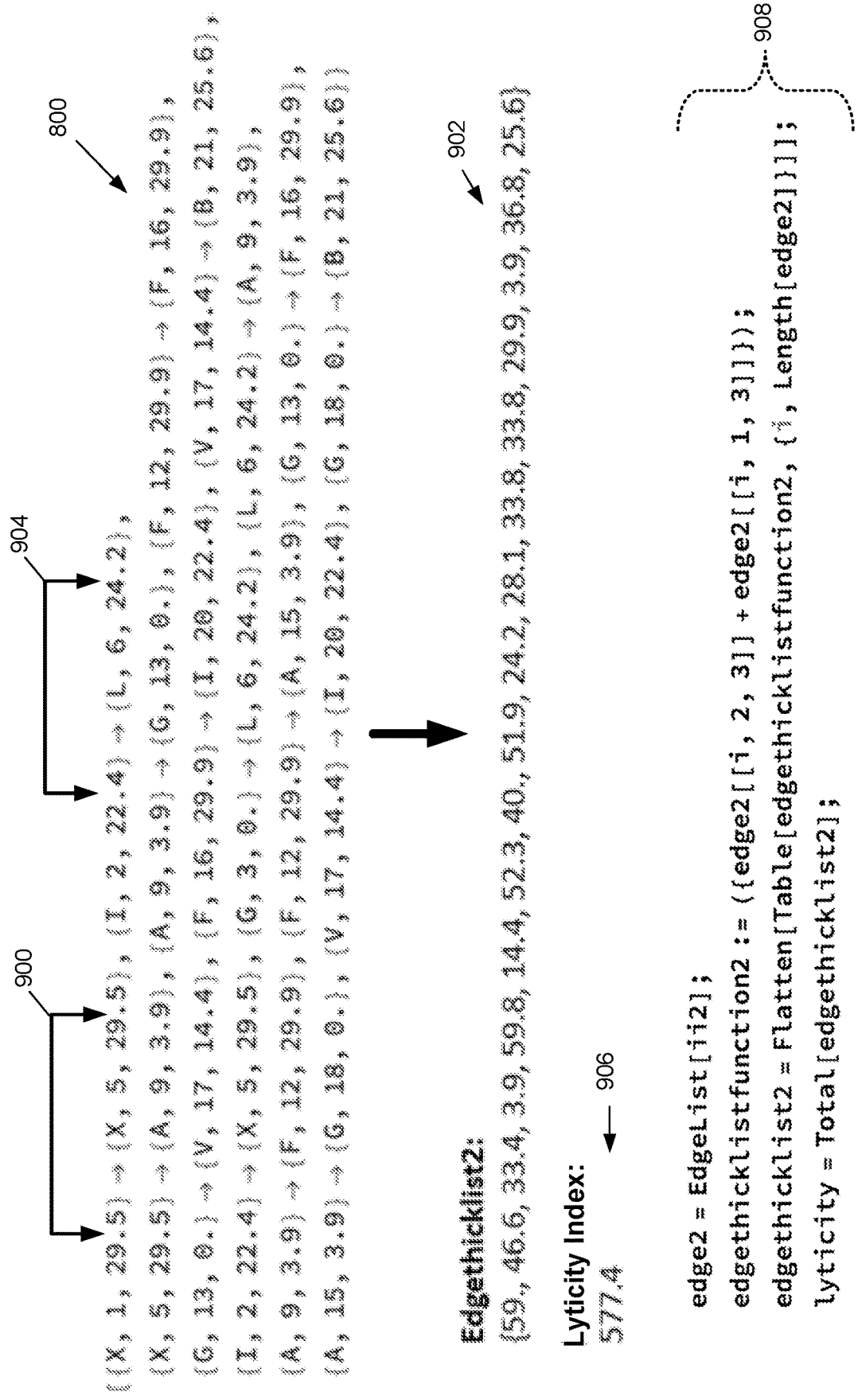
FIG. 9 illustrates producing a metric for characterizing relationship groups and corresponding executable instructions.

Referring to FIG. 9, upon producing the filtered data structure 800, the peptide manager 200 can execute operations; for example, one or more metrics may be determined for assisting the researcher in attaining a better understanding of the peptide sequence. Such metrics could be reviewed alone or in combination with one or more graphical representations of the peptide sequence. In this example, hydrophobicity values of the amino acids in each remaining relationship group are summed to attain a lyticity index. For example, the hydrophobicity values of the two amino acids of the first relationship group (highlighted with bracket 900) are summed (29.5+29.5=59) and stored in a first element of a vector 902 (labeled "Edgethicklist2"). Similarly the hydrophobicity values of the two amino acids in the second relationship group (highlighted with bracket 904) are summed (22.4+24.2=46.6) and are stored in a second element of the Edgethicklist2 vector 902. The peptide manager 200 continues to sum the hydrophobicity values of the relationship groups and store the values in elements of the vector 902. In this case, the vector 902 includes seventeen elements, one for each of the seventeen relationship groups.

To calculate the metric, e.g., a lyticity index 906, the peptide manager 200 computes the sum of the elements of the vector 902. In this example, the lyticity index 906 has a value of 577.4. In general, hydrophobic patches in peptides with alpha-helical structure correspond to increased lytic activity. As such, the lyticity index 906, which is representative of the amount and degree of hydrophobic amino acid interactions in the peptide, is a metric that increases with lytic activity. The lyticity index 906 has the advantage of giving researchers a single quantitative value for a peptide that serves as an indicator of a peptide's toxicity. To perform these operations, various types of executable instructions may be employed; for example, instructions 908 may be used by the peptide manager 200 to determine the lyticity index from the hydrophobicity values of the relationship groups.

Figure 10:
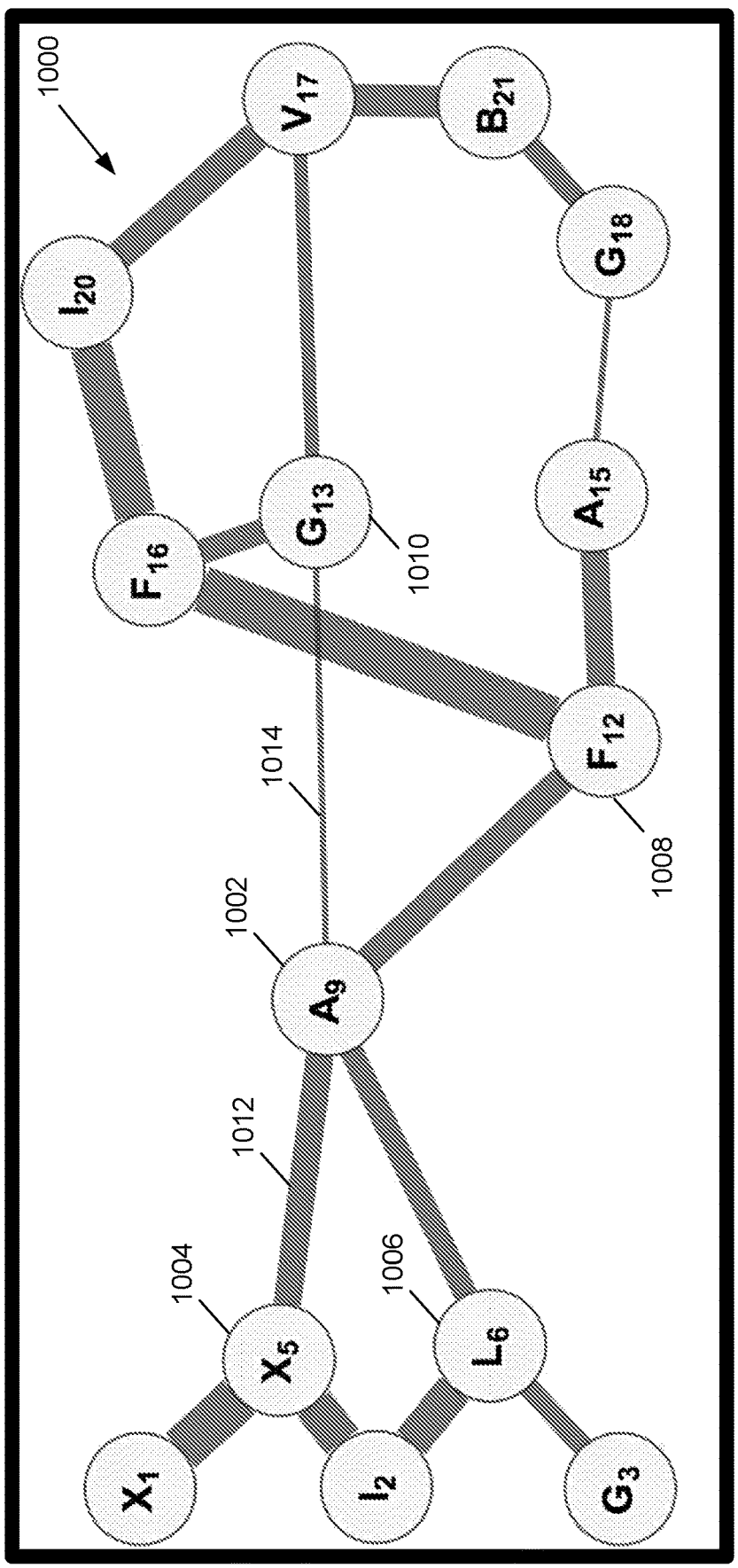
FIG. 10 is a network map representation of a peptide sequence.

Referring to FIG. 10, along with determining one or metrics such as the lyticity index (shown in FIG. 9), the peptide manager 200 produces a visual representation of the peptide sequence using the information from the filtered data structure 800 (shown in FIG. 8). As illustrated in this example, a network map representation 1000 (similar to the representation of FIG. 2) includes nodes that represent each hydrophobic amino acid included in the peptide sequence. To assist the viewer, each node includes information associated with the respective amino acid; for example, an identifier of amino acid (e.g., "X", "I", "G", "K", etc.) along with the hydrophobic amino acid's position in the peptide sequence (e.g., "1", "2", "3", "5", . . . , "21") is presented in each node. In this example, each distinct amino acid (from the filtered data structure 800) is represented once as a single node. If the amino acid is part of multiple relationship groups, the node representing the amino acid has multiple edges that connect to nodes representing other amino acids to form the corresponding relationship groups (e.g., i+3 and i+4 relationship groups). For example, relationship groups that include node 1002 (that represents amino acid "A" in the ninth position of the peptide sequence) are illustrated by connections with node 1004 (that represents amino acid "X" in the fifth position of the peptide sequence), node 1006 (that represents amino acid "L" in the sixth position of the peptide sequence), node 1008 (that represents amino acid "F" in the twelfth position of the peptide sequence), and node 1010 (that represents amino acid "G" in the thirteenth position of the peptide sequence). Each relationship group is represented by a graphical edge that connects the two nodes of the group. Additionally, each edge is represented as having a graphical characteristic (e.g., thickness) that is proportional to the sum of the hydrophobicity values of the amino acids being represented by the connected nodes. For example, an edge 1012 connecting nodes 1002 and 1004 is relatively thick to represent a large sum of hydrophobicity values (e.g., 33.4) while an edge 1014 is thinner to represent a comparatively smaller sum hydrophobicity values (e.g., 3.9).

In some implementations, the positioning of the nodes in the network map representation 1000 can be determined based on one or more criteria. For example, in some cases, the nodes may be placed to minimize the total length of the edges between nodes. In some cases, the nodes may be placed to minimize the number of intersections between edges. In some cases, the nodes may be placed such that they are always farther than a threshold distance from the nearest node. In some cases, a combination of these criteria, and/or additional criteria can be used to determining the positioning of each node.

In some implementations, the network map representation 1000 may be interactive, enabling a user to control the positioning of nodes. For example, in some cases, the user may be able to click-and-drag a node to a new location, while the network map representation 1000 maintains the edges between nodes. This may provide the advantage of allowing a user to customize the shape of the network map representation 1000 by creating a configuration more conducive to their exploration of the interactions between amino acids in the peptide sequence of interest.

By such a presentation, the network map representation 1000 is able to clearly display all of the amino acids and hydrophobic interactions of a peptide sequence in a two-dimensional representation, including interactions between closely proximal amino acids. Furthermore, the edge thicknesses give a clear visual representation of the relative hydrophobicity of each interaction. The network map representation 1000 also provides researchers with a sense of the amino acids with the most hydrophobic interactions, such as amino acid $A_9$ (represented by the node 1002), which may serve as useful targets of interest for disrupting large hydrophobic patches of the peptide 106. Additionally, to further assist the researcher, the lyticity index 906 (e.g., value 577.4) can be presented with the network map representation 1000 to provide an indication of the peptide's toxicity (as presented in FIG. 2).

While the network map representation 1000 is described as a two-dimensional representation, in some cases, it can be presented as a three-dimensional representation. In such cases, the nodes may be positioned in a three-dimensional environment according to one or more of the criteria described above. The three-dimensional environment may be interactive, allowing the user to rotate, zoom, and pan in order to view the peptide from different perspectives. Furthermore, as described above, the network map representation 1000 may itself be interactive, enabling a user to manually control the positioning of the nodes within the three-dimensional environment.

Figure 11:
FIG. 11 is a listing of instructions for producing a network map representation of a peptide sequence.

The peptide manager 200 may employ one or more techniques to prepare a visual representation such as the network map representation 1000. Referring to FIG. 11, a listing 1100 of exemplary executable instructions is shown that can be used by the peptide manager 200 to produce the network map representation. Along with instructions for producing such visual representations, the peptide manager 200 can provide other functionality to assist the researcher; for example, referring to FIG. 12, a function call 1200 may be employed to generate a user prompt (e.g., the interface 300 shown in FIG. 3), which prompts a user to input a peptide of interest. In this particular example, a single function initiates execution of the operations that leads to the selection of a peptide, presentation of the visual representation (e.g., a network map representation of the peptide, the lyticity index of the peptide,), etc. Additional functionality can also be initiated by such a function; for example, storing, cataloging, retrieval, etc., of peptide information, representations, etc. may be initiated by one or more function calls.

Figure 13:
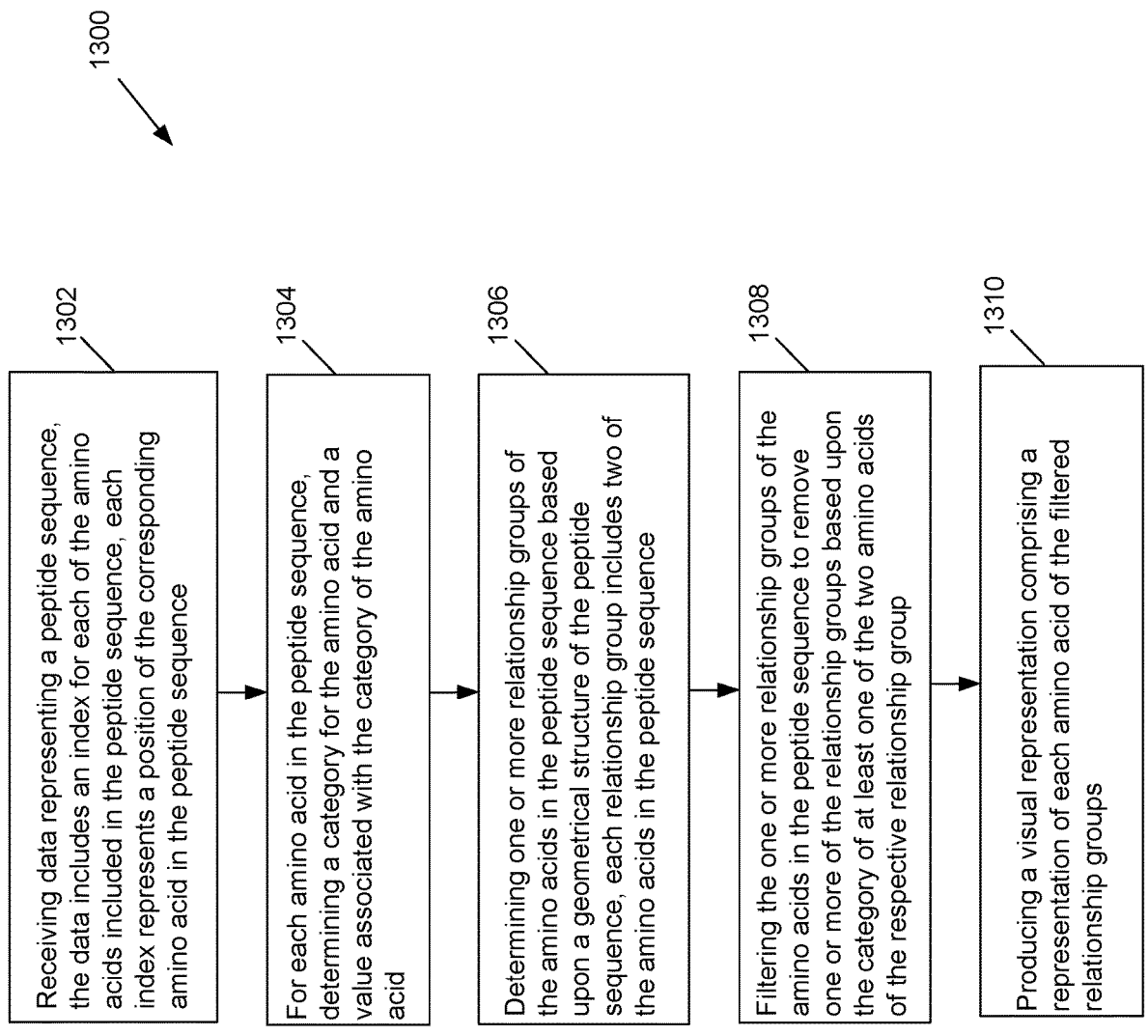
FIG. 13 is an example flow chart of operations of a peptide manager.

Referring to FIG. 13, a flowchart 1300 represents operations of a peptide manager (e.g., the peptide manager 200 shown in FIG. 2). Operations of the peptide manager are typically executed by a single computing device (e.g., the computer system 202); however, operations of the peptide manager may be executed by multiple computing devices. For example, the peptide manager may be an application program that is executed for use by one computing device. In some arrangements, the peptide manager may be accessible by multiple computing devices (e.g., via a cloud service) and executed by one computing device (e.g., a server at the cloud service) or multiple computing devices. Along with being executed at a single site (e.g., a peptide research facility, a cloud service site, etc.), the peptide manager may be executed in a distributed manner among two or more locations.

Operations of the peptide manager may include receiving 1302 data representing a peptide sequence, the data includes an index for each amino acid included in the peptide sequence. Each index represents a position of the corresponding amino acid in the peptide sequence. For example, based upon a peptide being select by a user (e.g., using the interface 300 shown in FIG. 3), data can be retrieved that represents a vector of amino acids included in a peptide sequence. The position of the amino acid in the vector can correspond to the position of the amino acid in the peptide sequence. Retrieved data may also include other information such as values representing the hydrophobicity of the amino acids (as provided by the instructions shown in FIG. 4). Operations of the peptide manager may also include, for each amino acid in the peptide sequence, determining 1304 a category for the amino acid and a value associated with the category for the amino acid. For example, from retrieved hydrophobicity values the peptide manager can determine if each amino acid is a member of a hydrophobic category or a hydrophilic category. Operations of the peptide manager may also include, determining 1306 one or more relationship groups of the amino acids in the peptide sequence based upon a geometrical structure of the peptide sequence. Each relationship group includes two of the amino acids in the peptide sequence. For example, relationship groups can be determined based upon the separation of the amino acids in the peptide sequence. In one arrangement, amino acids separated by two amino acids (e.g., i+3 relationship groups) and amino acids separated by three amino acids (e.g., i+4 relationship groups) of the peptide sequence may be identified. Operations of the peptide manager may also include filtering 1308 the one or more relationship groups of the amino acids in the peptide sequence to remove one or more of the relationship groups based upon the category of at least one of the two amino acids of the respective relationship group. For example, the i+3 and i+4 relationship groups may be filtered for removing any relationship group that includes a hydrophilic amino acid. Operations of the peptide manager may also include producing 1310 a visual representation comprising a representation of each amino acid of the filtered relationship groups. For example, as illustrated in FIG. 10, a network map representation may be produced that presents a representation of all the amino acids in hydrophobic relationship groups included in the peptide sequence. In some instances, additional information may be included in the visual representation; for example, one or more metrics such as a lyticity index may be presented to provide the viewer with a measure of the toxicity of the presented peptide along with the overall structure and interactions of the hydrophobic amino acids.

Figure 14A:
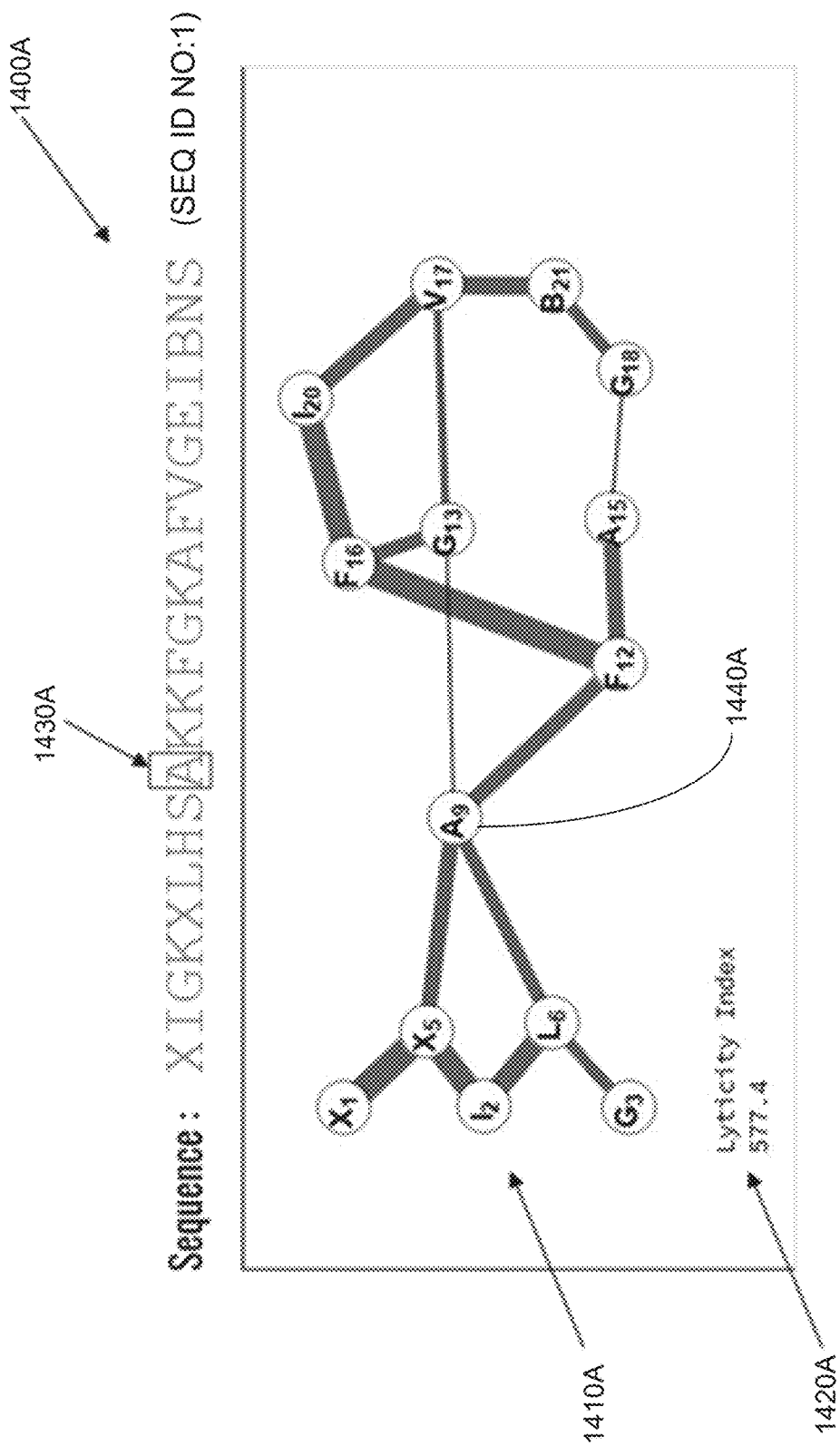
FIG. 14A is an example peptide sequence (SEQ ID NO:1) and its corresponding network map representation.

In some implementations, peptide manager 200 can be configured not only to create a visual representation of a peptide sequence, but also to create a visual representation of the effects of mutating the peptide sequence. For example, referring to FIG. 14A, the network map representation 1410A for an example peptide sequence (SEQ ID NO:1) 1400A is shown along with the calculated lyticity index 1420A, which has a value of 577.4. In this case, the example peptide sequence 1400A is "XIGKXLH-SAKKFGKAFVGEIBNS", which, for the purposes of demonstration, is the same peptide sequence used for the description of FIGS. 4-10 above.

Figure 14B:
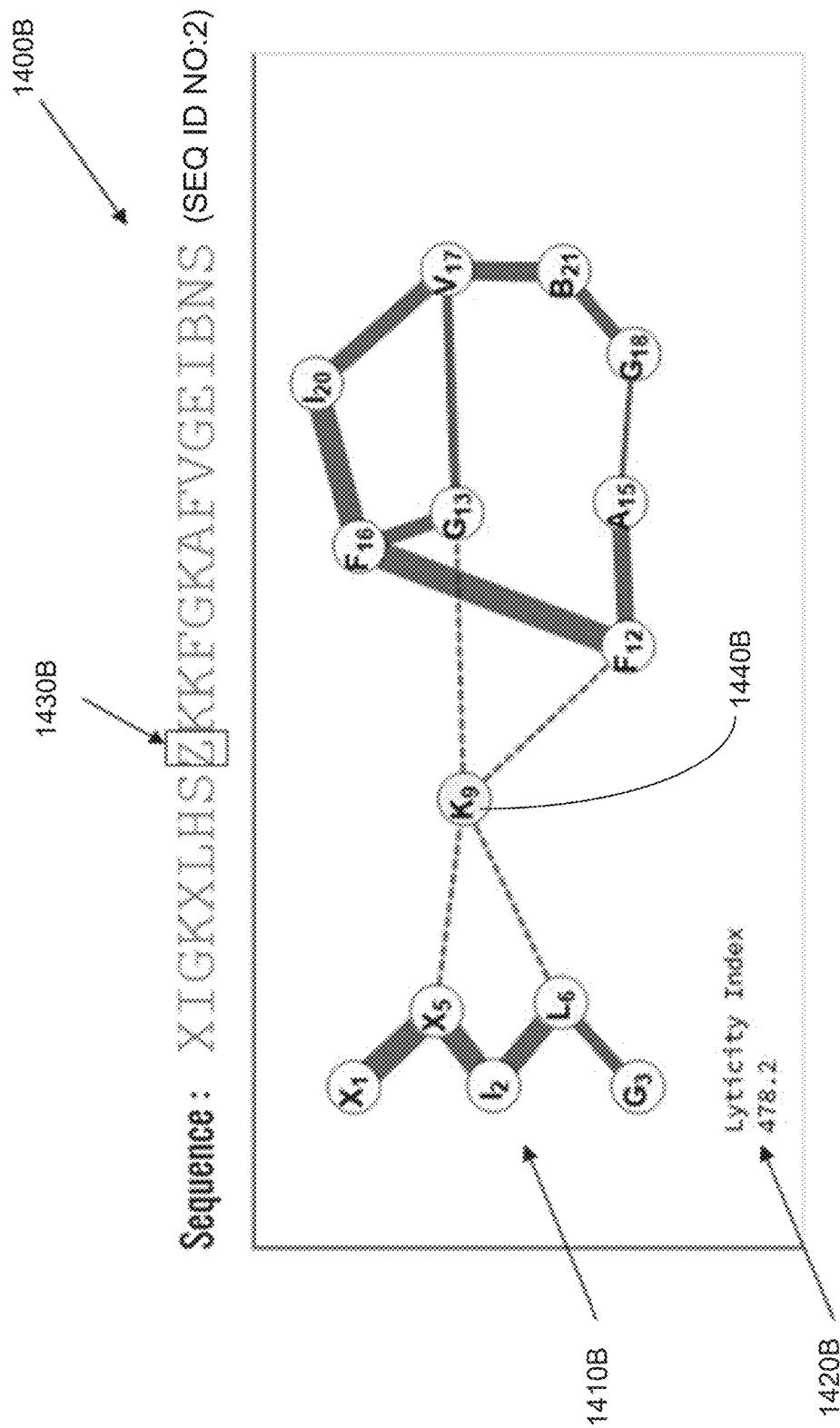
FIG. 14B is a modified peptide sequence (SEQ ID NO:2) and its corresponding network map representation.

In some cases, a user may be interested in visualizing the changes to a hydrophobicity network map in the case of a mutation. For example, a user may desire to visualize the effect of replacing a hydrophobic amino acid such as "A" in the 9th index of peptide sequence 1400A with a hydrophilic residue. Referring to FIG. 14B, in order to observe this effect, the user can modify the input peptide sequence to "XIGKXLHSZKKFGKAFVGEIBNS" (1400B), replacing the "A" at the 9th index (1430A) with a "Z" (1430B). In this case, the character "Z" serves as an indicator that the user would like to substitute a hydrophilic amino acid (e.g., lysine) at this index of the peptide sequence. In other implementations, the peptide manager 200 can be configured to recognize other codes or indicators.

Referring still to FIG. 14B, in response to receiving the modified peptide sequence (SEQ ID NO:2) 1400B, the peptide manager 200 generates the updated network map representation 1410B. As shown, the $A_9$ node (1440A) has been replaced with a $K_9$ node (1440B), representing a lysine residue at the 9th index of the peptide sequence. In some cases, other hydrophilic amino acids may be used. Furthermore, referring to both FIG. 14A and FIG. 14B, the edges connecting the $A_9$ node to other nodes in the network map representation 1410A have been replaced with dotted lines in the updated network map representation 1410B. In this case, the dotted lines provide a visual representation of the disruption to the hydrophobic interactions that result from replacing the $A_9$ node with a $K_9$ node. The user is also presented with an updated lyticity index value (1420B) of 478.2, which is lower than the original lyticity index value (1420A) of 577.4. In this case, the lyticity index value is reduced because the edges connecting to the $A_9$ node in network map representation 1410A have been replaced with edges that do not contribute to the lyticity index. This visual comparison of the original peptide sequence 1400A with the mutated, or modified, peptide sequence 1400B can assist the user in understanding the effects of various modification to a peptide's hydrophobic network.

Along with producing visual representations of the peptide sequences and calculating metrics, the peptide manager 200 may process the peptide information for other functionality. For example, through evaluation, characterization, etc. particular peptides, amino acids, relationship groups, etc. may be identified that could be helpful in peptide development. The peptide manager 200 can provide such functionality by using peptide information with machine learning techniques to recommend amino acid substitutions, deletions, insertions, etc. Machine learning techniques can be used to identify peptides (or other information such as amino acids, relationship groups, etc.) for development efforts, a recommendation service, etc. For example, through the use of these techniques libraries may be created and used to detect particular aspects of peptides and provide suggestions. Along with information associated with peptides (e.g., identified amino acids, hydrophobicity data, etc.), processed data may be used in the machine learning techniques (e.g., to train a machine learning system). For example, processed data such as one or more calculated metrics (e.g., lyticity indices) may be employed for system training. Experimental data can also be used for training a machine learning system. Various data sources can provide this information: local storage (e.g., storage device 304) and/or remote storage locations (e.g., accessible by one or more networks such as the Internet).

By training the machine learning system, the peptide manager 200 is capable of contributing to a number of functions. For example, characteristics, capabilities, etc. of peptides may be determined in advance by the peptide manager 200 for future use. For example, as new peptides are developed, the peptide manager 200 may categorize the new peptides and determine similarities with these peptides and previously analyzed peptides. Such preparation work could improve efficiency in peptide development. The peptide manager 200 can also manage data that represents similarities (or dissimilarities) among the peptide sequences, characteristics of the peptides, amino acids present in the peptides, etc. As such, similar peptide sequences may be quickly identified and provided to a requesting researcher's computing device. In one arrangement, a database (e.g., stored on storage device 304) includes records that represent the similarities (or dissimilarities) among peptides and is accessible by the peptide manager 200. In some instances, the similarity (or dissimilarity) information may be monitored, tracked, etc. by the peptide manager 200. For example, records may be stored that reflect particular peptides that have been requested, identified by the machine learning system, etc.

One or more forms of artificial intelligence, such as machine learning, can be employed such that a computing process or device may learn to determine peptide similarities (or dissimilarities) from training data, without being explicitly programmed for the task. Using this training data, machine learning may employ techniques such as regression to estimate peptide similarities. To produce such estimates, one or more quantities may be defined as a measure of peptide similarity. For example, amino acids, group relationships, hydrophobicity, lyticity index values, etc. may be used to define differences between two peptides. One or more conventions may be utilized; for example, a pair of peptides that have relatively close lyticity index values can be considered similar. Alternatively a large difference in lyticity index values can be indicative of peptides being considered different. As such, upon being trained, a learning machine may be capable of outputting a numerical value that represents the difference in lyticity index values of two peptides.

To implement such an environment, one or more machine learning techniques may be employed. For example, supervised learning techniques may be implemented in which training is based on a desired output that is known for an input. Supervised learning can be considered an attempt to map inputs to outputs and then estimate outputs for previously unused inputs. Unsupervised learning techniques may also be used in which training is provided from known inputs but unknown outputs. Reinforcement learning techniques may also be employed in which the system can be considered as learning from consequences of actions taken (e.g., inputs values are known and feedback provides a performance measure). In some arrangements, the implemented technique may employ two or more of these methodologies. For example, the learning applied can be considered as not exactly supervised learning since the level of difference between two peptides can be considered unknown prior to executing computations. While the difference level is unknown, the implemented techniques can check the computed peptide differences in concert with comparing lyticity index values. By using both information sources regarding peptide similarity, a reinforcement learning technique can be considered as being implemented.

In some arrangements, neural network techniques may be implemented using the peptide information (e.g., vectors of numerical values that represent features of the peptides) to invoke training algorithms for automatically learning the peptides and related information. Such neural networks typically employ a number of layers. Once the layers and number of units for each layer is defined, weights and thresholds of the neural network are typically set to minimize the prediction error through training of the network. Such techniques for minimizing error can be considered as fitting a model (represented by the network) to the training data. By using the peptide information (e.g., peptide features), a function may be defined that quantifies error (e.g., a squared error function used in regression techniques). By minimizing error, a neural network may be developed that is capable of estimating amino acid recommendations (e.g., for substitution, deletion, insertion, etc.), peptide similarity, etc. Other factors may also be accounted for during neutral network development. For example, a model may too closely attempt to fit data (e.g., fitting a curve to the extent that the modeling of an overall function is degraded). Such overfitting of a neural network may occur during the model training and one or more techniques may be implements to reduce its effects.

A variety of peptide features may be used for training and using a machine learning system. For example, tens of features may be calculated for each peptide. Features may include, for example, the amino acids found in peptide, most common amino acids found in peptides, amino acid categories (e.g., hydrophobic, hydrophilic, etc.), amino acid relationship groups, hydrophobicity of amino acids, hydrophobicity of relationship groups, etc. In some arrangements, peptide features may be processed prior to being used for machine training (or for use by a trained machine to determine amino acid recommendations). For example, a vector that represents a collection of peptide features may be normalized so that training data used can be considered as being placed on an equal basis (and one or more particular peptide features are not overly emphasized). Such normalizing operations may take many forms. For example, an estimated value (e.g., average) and standard deviation (or variance) may be calculated for each feature. Once these quantities are calculated (e.g., the average and standard deviation), each feature is normalized using the data.

Once trained, the peptide manager 200 may be used to recommend amino acids (e.g., for substitution, deletion, insertion). The peptide manager 200 can calculate and compare, for example, features such as lyticity index values to determine amino acid recommendations. Along with determining amino acid recommendations, the peptide manager 200 may provide other functionality. For example, the peptide manager 200 may also initiate the storage of data that represents peptides, amino acid recommendations, preferences of researchers using the peptide manager 300, etc. Storing such data generally allows the information to be quickly retrieved rather than being recalculated. For example, for peptide (represented in data stored in the storage device 304), a list of recommended amino acids may be produced and stored for quick retrieval. As new peptides appear (e.g., are developed, identified, etc.) operations may be executed to quickly present recommended amino acids, update a peptide database, etc. Techniques such as batch processing may be implemented for determining amino acid recommendations relatively large numbers of peptides. In some situations multiple new peptides may be introduced together and techniques may be employed to efficiently recommend amino acids from the machine learning system. For example, trained on previously known peptides and associated amino acids and operations executed to recommend amino acids for each of the new peptides. By implementing batch processing or other similar techniques, updating of databases (to reflect new peptides) may be executed during less busy time periods (e.g., overnight).

Figure 15:
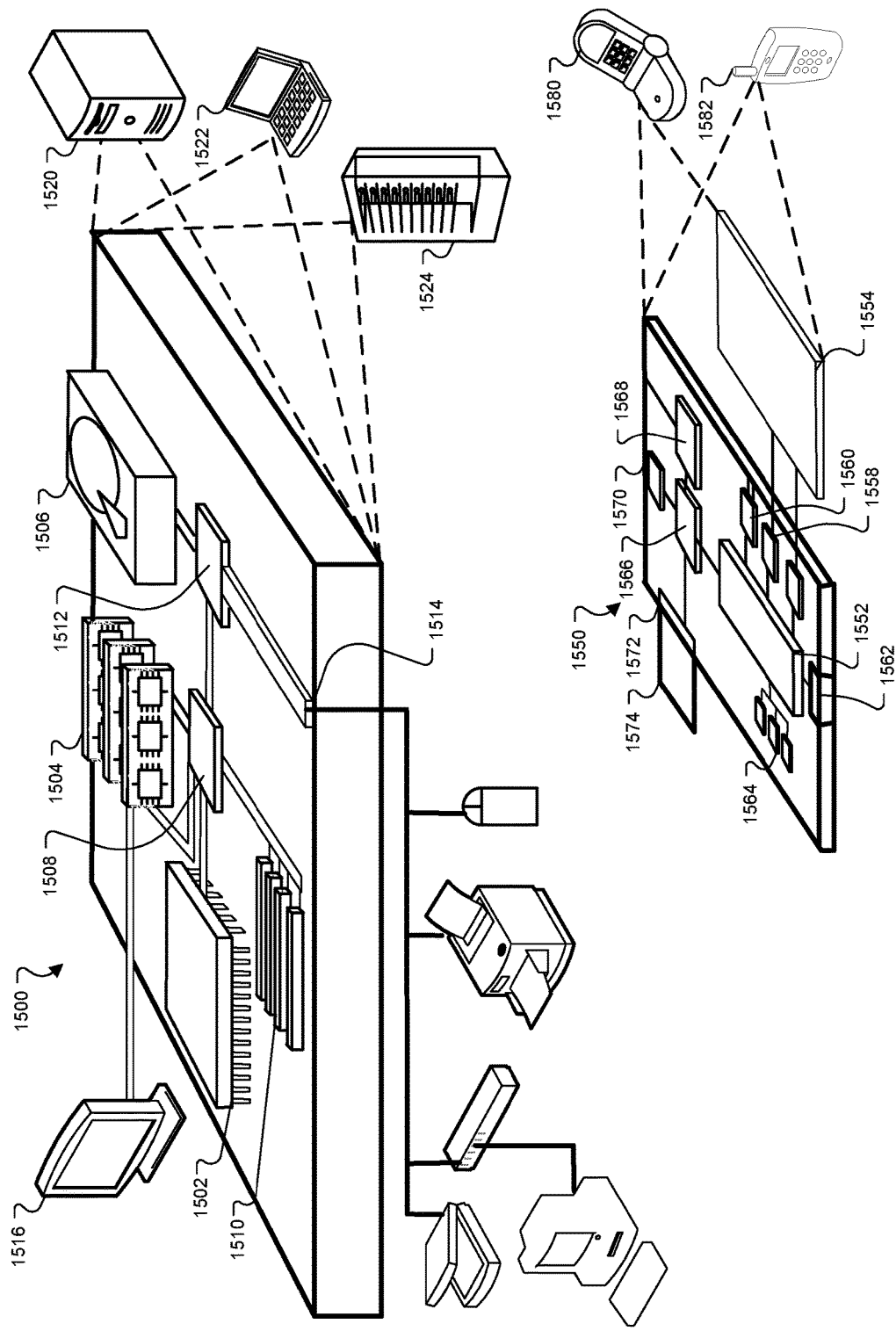
FIG. 15 illustrates an example of a computing device and a mobile computing device that can be used to implement the techniques described here.

FIG. 15 shows an example of example computer device 1500 and example mobile computer device 1550, which can be used to implement the techniques described herein. For example, a portion or all of the operations of the peptide manager 200 (shown in FIG. 2) may be executed by the computer device 1500 and/or the mobile computer device 1550. Computing device 1500 is intended to represent various forms of digital computers, including, e.g., laptops, desktops, workstations, personal digital assistants, servers, blade servers, mainframes, and other appropriate computers. Computing device 1550 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 1500 includes processor 1502, memory 1504, storage device 1506, high-speed interface 1508 connecting to memory 1504 and high-speed expansion ports 1510, and low-speed interface 1512 connecting to low-speed bus 1514 and storage device 1506. Each of components 1502, 1504, 1506, 1508, 1510, and 1512, are interconnected using various busses, and can be mounted on a common motherboard or in other manners as appropriate. Processor 1502 can process instructions for execution within computing device 1500, including instructions stored in memory 1504 or on storage device 1506 to display graphical data for a GUI on an external input/output device, including, e.g., display 1516 coupled to high-speed interface 1508. In other implementations, multiple processors and/or multiple busses can be used, as appropriate, along with multiple memories and types of memory. Also, multiple computing devices 1500 can be connected, with each device providing portions of the necessary operations (e.g., as a server bank, a group of blade servers, or a multi-processor system).

Memory 1504 stores data within computing device 1500. In one implementation, memory 1504 is a volatile memory unit or units. In another implementation, memory 1504 is a non-volatile memory unit or units. Memory 1504 also can be another form of computer-readable medium (e.g., a magnetic or optical disk. Memory 1504 may be non-transitory.).

Storage device 1506 is capable of providing mass storage for computing device 1500. In one implementation, storage device 1506 can be or contain a computer-readable medium (e.g., a floppy disk device, a hard disk device, an optical disk device, or a tape device, a flash memory or other similar solid state memory device, or an array of devices, such as devices in a storage area network or other configurations.) A computer program product can be tangibly embodied in a data carrier. The computer program product also can contain instructions that, when executed, perform one or more methods (e.g., those described above.) The data carrier is a computer- or machine-readable medium, (e.g., memory 1504, storage device 1506, memory on processor 1502, and the like.)

High-speed controller 1508 manages bandwidth-intensive operations for computing device 1500, while low-speed controller 1512 manages lower bandwidth-intensive operations. Such allocation of functions is an example only. In one implementation, high-speed controller 1508 is coupled to memory 1504, display 1516 (e.g., through a graphics processor or accelerator), and to high-speed expansion ports 1510, which can accept various expansion cards (not shown). In the implementation, low-speed controller 1512 is coupled to storage device 1506 and low-speed expansion port 1514. The low-speed expansion port, which can include various communication ports (e.g., USB, Bluetooth®, Ethernet, wireless Ethernet), can be coupled to one or more input/output devices, (e.g., a keyboard, a pointing device, a scanner, or a networking device including a switch or router, e.g., through a network adapter.).

Computing device 1500 can be implemented in a number of different forms, as shown in the figure. For example, it can be implemented as standard server 1520, or multiple times in a group of such servers. It also can be implemented as part of rack server system 1524. In addition or as an alternative, it can be implemented in a personal computer (e.g., laptop computer 1522.) In some examples, components from computing device 1500 can be combined with other components in a mobile device (not shown), e.g., device 1550. Each of such devices can contain one or more of computing device 1500, 1550, and an entire system can be made up of multiple computing devices 1500, 1550 communicating with each other.

Computing device 1550 includes processor 1552, memory 1564, an input/output device (e.g., display 1554, communication interface 1566, and transceiver 1568) among other components. Device 1550 also can be provided with a storage device, (e.g., a microdrive or other device) to provide additional storage. Each of components 1550, 1552, 1564, 1554, 1566, and 1568, are interconnected using various buses, and several of the components can be mounted on a common motherboard or in other manners as appropriate.

Processor 1552 can execute instructions within computing device 1550, including instructions stored in memory 1564. The processor can be implemented as a chipset of chips that include separate and multiple analog and digital processors. The processor can provide, for example, for coordination of the other components of device 1550, e.g., control of user interfaces, applications run by device 1550, and wireless communication by device 1550.

Processor 1552 can communicate with a user through control interface 1558 and display interface 1556 coupled to display 1554. Display 1554 can be, for example, a TFT LCD (Thin-Film-Transistor Liquid Crystal Display) or an OLED (Organic Light Emitting Diode) display, or other appropriate display technology. Display interface 1556 can comprise appropriate circuitry for driving display 1554 to present graphical and other data to a user. Control interface 1558 can receive commands from a user and convert them for submission to processor 1552. In addition, external interface 1562 can communicate with processor 1542, so as to enable near area communication of device 1550 with other devices. External interface 1562 can provide, for example, for wired communication in some implementations, or for wireless communication in other implementations, and multiple interfaces also can be used.

Memory 1564 stores data within computing device 1550. Memory 1564 can be implemented as one or more of a computer-readable medium or media, a volatile memory unit or units, or a non-volatile memory unit or units. Expansion memory 1574 also can be provided and connected to device 1550 through expansion interface 1572, which can include, for example, a SIMM (Single In Line Memory Module) card interface. Such expansion memory 1574 can provide extra storage space for device 1550, or also can store applications or other data for device 1550. Specifically, expansion memory 1574 can include instructions to carry out or supplement the processes described above, and can include secure data also. Thus, for example, expansion memory 1574 can be provided as a security module for device 1550, and can be programmed with instructions that permit secure use of device 1550. In addition, secure applications can be provided through the SIMM cards, along with additional data, (e.g., placing identifying data on the SIMM card in a non-hackable manner.).

The memory can include, for example, flash memory and/or NVRAM memory, as discussed below. In one implementation, a computer program product is tangibly embodied in a data carrier. The computer program product contains instructions that, when executed, perform one or more methods, e.g., those described above. The data carrier is a computer- or machine-readable medium (e.g., memory 1564, expansion memory 1574, and/or memory on processor 1552), which can be received, for example, over transceiver 1568 or external interface 1562.

Device 1550 can communicate wirelessly through communication interface 1566, which can include digital signal processing circuitry where necessary. Communication interface 1566 can provide for communications under various modes or protocols (e.g., GSM voice calls, SMS, EMS, or MMS messaging, CDMA, TDMA, PDC, WCDMA, CDMA2000, or GPRS, among others.) Such communication can occur, for example, through radio-frequency transceiver 1568. In addition, short-range communication can occur, e.g., using a Bluetooth®, WiFi, or other such transceiver (not shown). In addition, GPS (Global Positioning System) receiver module 1570 can provide additional navigation- and location-related wireless data to device 1550, which can be used as appropriate by applications running on device 1550. Sensors and modules such as cameras, microphones, compasses, accelerators (for orientation sensing), etc. may be included in the device.

Device 1550 also can communicate audibly using audio codec 1560, which can receive spoken data from a user and convert it to usable digital data. Audio codec 1560 can likewise generate audible sound for a user, (e.g., through a speaker in a handset of device 1550.) Such sound can include sound from voice telephone calls, can include recorded sound (e.g., voice messages, music files, and the like) and also can include sound generated by applications operating on device 1550.

Computing device 1550 can be implemented in a number of different forms, as shown in the figure. For example, it can be implemented as cellular telephone 1580. It also can be implemented as part of smartphone 1582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor. The programmable processor can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a device for displaying data to the user (e.g., a CRT (cathode ray tube) or LCD (liquid crystal display) monitor), and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such back end, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other. For example, in some implementations, the functionality of the peptide manager 200 executed by computer system 202 (e.g., a server) can be provided as a web application. For example, an external computer system (e.g., a client) may, over the Web, request computer system 202 to execute at least a portion of the functionality of the peptide manager 200. In response, the computer system 202 can execute the peptide manager 200 and send data corresponding to a resulting network map representation to the client for presentation at the external computer system.

In some implementations, the engines described herein can be separated, combined or incorporated into a single or combined engine. The engines depicted in the figures are not intended to limit the systems described here to the software architectures shown in the figures.

A number of embodiments have been described. Nevertheless, it will be understood that various modifications can be made without departing from the spirit and scope of the processes and techniques described herein. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method comprising:

receiving data representing a first antimicrobial peptide sequence;

receiving data representing a second antimicrobial peptide sequence that comprises one or more modifications of the first antimicrobial peptide sequence, wherein the data includes an index for each amino acid included in the second antimicrobial peptide sequence, and wherein each index represents a position of the corresponding amino acid in the second antimicrobial peptide sequence;

for each amino acid in the second antimicrobial peptide sequence, determining a category for the amino acid and a value associated with the category for the amino acid;

determining one or more relationship groups of the amino acids in the second antimicrobial peptide sequence based upon a geometrical structure of the second antimicrobial peptide sequence, wherein each relationship group includes two of the amino acids in the second antimicrobial peptide sequence;

filtering the one or more relationship groups of the amino acids in the second antimicrobial peptide sequence to remove one or more of the relationship groups if at least one of the two amino acids of the respective relationship group is hydrophilic;

producing a visual representation of hydrophobic interactions of the second antimicrobial peptide sequence, the visual representation comprising a network map with nodes and edges, wherein each node represents an individual amino acid of the filtered relationship groups, and wherein the edges represent the filtered relationship groups;

computing a lyticity metric for the second antimicrobial peptide sequence corresponding to the visual representation of hydrophobic interactions of the second antimicrobial peptide sequence;

comparing the lyticity metric for the second antimicrobial peptide sequence with a lyticity metric for the first antimicrobial peptide sequence;

determining that the lyticity metric for the second antimicrobial peptide sequence is less than the lyticity metric for the first antimicrobial peptide sequence; and in response to determining that the lyticity metric for the second antimicrobial peptide sequence is less than the lyticity metric for the first antimicrobial peptide sequence, synthesizing a peptide in accordance with the second antimicrobial peptide sequence, wherein the synthesized peptide has a lower toxicity than another peptide corresponding to the first antimicrobial peptide sequence.

2. The method of claim 1, further comprising:

determining a peptide index from the values associated with the amino acids of the filtered relationship groups, wherein the visual representation represents the peptide index.

3. The method of claim 2, wherein determining the peptide index comprises summing values associated with amino acids for each filtered relationship group.

4. The method of claim 2, wherein determining the peptide index comprises summing values associated with amino acids for all of the filtered relationship groups.

5. The method of claim 1, wherein the category for the amino acid includes one of hydrophobicity and hydrophilicity.

6. The method of claim 1, wherein the value associated with the category for the amino acid includes one of a level of hydrophobicity and a level of hydrophilicity.

7. The method of claim 1, wherein determining one or more relationship groups of the amino acids in the second antimicrobial peptide sequence based upon a geometrical structure of the second antimicrobial peptide sequence comprises determining two amino acids separated by two amino acids.

8. The method of claim 1, wherein determining one or more relationship groups of the amino acids in the second antimicrobial peptide sequence based upon a geometrical structure of the second antimicrobial peptide sequence comprises determining two amino acids separated by three amino acids.

9. The method of claim 1, further comprising experimentally testing at least one of a lytic activity or an antimicrobial potency of the synthesized peptide.

10. The method of claim 1, comprising:
   obtaining experimental data about one or more peptide features of a plurality of additional peptides;
   training a machine learning model, using the experimental data, to recommend amino acid substitutions, deletions, or insertions to the plurality of additional peptides to achieve target peptide features;
   utilizing the machine learning model to recommend a modification to the second antimicrobial peptide sequence; and
   producing a modified visual representation corresponding to the recommended modification to the second antimicrobial peptide sequence.

11. The method of claim 1, wherein a visual characteristic of the edges represents a hydrophobicity of the filtered relationship groups.

12. The method of claim 11, wherein the visual characteristic is an edge thickness.

* * * * *